US011951027B2

(12) United States Patent
Gildersleeve et al.

(10) Patent No.: US 11,951,027 B2
(45) Date of Patent: *Apr. 9, 2024

(54) CUSTOMIZABLE KNEE BRACE INTENDED FOR PATIENTS WITH OSTEOARTHRITIS

(71) Applicant: DJO, LLC, Carlsbad, CA (US)

(72) Inventors: Richard E Gildersleeve, Carlsbad, CA (US); Ian Kovacevich, Vista, CA (US); Nicholas Gomez, Vista, CA (US)

(73) Assignee: DJO, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/127,316

(22) Filed: Mar. 28, 2023

(65) Prior Publication Data
US 2023/0320884 A1  Oct. 12, 2023

Related U.S. Application Data

(63) Continuation of application No. 17/237,860, filed on Apr. 22, 2021, now Pat. No. 11,617,671, which is a
(Continued)

(51) Int. Cl.
*A61F 5/01* (2006.01)

(52) U.S. Cl.
CPC .... *A61F 5/0125* (2013.01); *A61F 2005/0134* (2013.01); *A61F 2005/0139* (2013.01);
(Continued)

(58) Field of Classification Search
CPC ........ A61F 5/01; A61F 5/0102; A61F 5/0104; A61F 5/0106; A61F 5/0123;
(Continued)

(56) References Cited

U.S. PATENT DOCUMENTS

| 3,581,741 A | 6/1971 | Rosman et al. |
| 4,193,395 A | 3/1980 | Gruber |

(Continued)

FOREIGN PATENT DOCUMENTS

| CN | 1163095 A | 10/1997 |
| CN | 102421394 A | 4/2012 |

(Continued)

OTHER PUBLICATIONS

International Search Report dated Jan. 12, 2017 for PCT Application No. PCT/US16/57133.
(Continued)

*Primary Examiner* — Michelle J Lee
*Assistant Examiner* — Robin Han
(74) *Attorney, Agent, or Firm* — Veros Legal Solutions, LLP

(57) ABSTRACT

A customizable knee brace for use in the treatment of osteoarthritis is provided. The customizable knee brace includes a lateral upright. The lateral upright includes at least a first semi-rigid support, a second semi-rigid support, and a hinge physically coupling the first semi-rigid support and the second semi-rigid support. The customizable knee brace further includes a thigh cuff constructed of formable material and coupled to the first semi-rigid support. The customizable knee brace further includes a shin cuff constructed of formable material and coupled to the second semi-rigid support. The customizable knee brace further includes an elastomeric web framework coupled to the lateral upright and configured to secure an area of a knee of a patient when wearing the customizable knee brace. The customizable knee brace further includes at least one tensioning element configured to adjust a tension of the elastomeric web framework.

20 Claims, 9 Drawing Sheets

Related U.S. Application Data continuation of application No. 15/294,110, filed on Oct. 14, 2016, now abandoned.

(60) Provisional application No. 62/241,989, filed on Oct. 15, 2015.

(52) U.S. Cl.
CPC .............. *A61F 2005/0172* (2013.01); *A61F 2005/0174* (2013.01); *A61F 2005/0179* (2013.01)

(58) Field of Classification Search
CPC ............ A61F 5/0125; A61F 2005/0134; A61F 2005/0137; A61F 2005/0139; A61F 2005/0172; A61F 2005/0174; A61F 2005/0176; A61F 2005/0179; A61F 2005/0181
USPC ..................................................... 602/16, 26
See application file for complete search history.

(56) References Cited

U.S. PATENT DOCUMENTS

| | | | |
|---|---|---|---|
| 4,928,670 A | | 5/1990 | DeLorenzo |
| 4,986,264 A | | 1/1991 | Miller |
| 4,991,571 A | * | 2/1991 | Kausek .................. A61F 5/0123 602/26 |
| 5,131,385 A | | 7/1992 | Kuehnegger et al. |
| 5,554,104 A | | 9/1996 | Grim |
| 5,891,071 A | | 4/1999 | Stearns et al. |
| 8,679,042 B2 | | 3/2014 | Kausek |
| 9,427,350 B1 | | 8/2016 | Clements |
| 11,617,671 B2 | | 4/2023 | Gildersleeve |
| 2004/0002674 A1 | | 1/2004 | Sterling |
| 2004/0054311 A1 | | 3/2004 | Sterling |
| 2006/0030804 A1 | | 2/2006 | Nordt et al. |
| 2006/0030806 A1 | | 2/2006 | Nordt et al. |
| 2007/0021706 A1 | | 1/2007 | Braunstein et al. |
| 2008/0039757 A1 | | 2/2008 | Nordt et al. |
| 2008/0208095 A1 | | 8/2008 | Kazmierczak et al. |
| 2009/0259156 A1 | | 10/2009 | Nordt et al. |
| 2009/0259196 A1 | | 10/2009 | Gratwohl et al. |
| 2011/0218471 A1 | | 9/2011 | Ingimundarson et al. |
| 2012/0101417 A1 | | 4/2012 | Joseph |
| 2014/0276302 A1 | | 9/2014 | Gildersleeve et al. |
| 2015/0150705 A1 | | 6/2015 | Capra et al. |
| 2017/0105865 A1 | | 4/2017 | Gildersleeve et al. |

FOREIGN PATENT DOCUMENTS

| | | |
|---|---|---|
| EP | 3362007 A1 | 8/2018 |
| JP | 5615849 B2 | 10/2014 |
| WO | 2013038709 A1 | 3/2013 |
| WO | 2017066632 A1 | 4/2017 |

OTHER PUBLICATIONS

Notice of Allowance Received for U.S. Appl. No. 17/237,860 dated Dec. 5, 2022, 12 pages.

* cited by examiner

CUSTOMIZABLE KNEE BRACE INTENDED FOR PATIENTS WITH OSTEOARTHRITIS

CROSS-REFERENCE TO RELATED APPLICATIONS

This application is a continuation of, and claims the benefit of, U.S. patent application Ser. No. 17/237,860, filed Apr. 22, 2021, and will issue as U.S. Pat. No. 11,617,671 on Apr. 4, 2023, which is a continuation of and claims the benefit of U.S. patent application Ser. No. 15/294,110, filed Oct. 14, 2016, now abandoned, which claims the benefit of U.S. Provisional Application No. 62/241,989, filed Oct. 15, 2015. The contents of each of the aforementioned patent applications are hereby incorporated by reference in their entireties.

BACKGROUND

Field of the Disclosure

Disclosed herein is a customizable knee brace intended for patients with osteoarthritis. Methods of treating a patient having osteoarthritis are likewise provided.

Description of the Related Technology

Osteoarthritis (OA), commonly known as wear-and-tear arthritis, is a condition in which the natural cushioning between joints wears away. Osteoarthritis is one of the most frequent causes of physical disability among adults, with over 20 million people in the United States having the disease. By 2030, it is estimated that 20% of all Americans, approximately 70 million people, will be at risk for osteoarthritis. A degenerative joint disease, osteoarthritis causes chronic pain in the affected joint when the joint is statically or dynamically loaded.

Primary osteoarthritis often affects weight bearing joints, such as the knee. Repetitive use of a joint, such as the knee, over time can irritate and inflame the cartilage, causing joint pain and swelling. Eventually, cartilage begins to degenerate and as cartilage is diminished, the bones of the knee joints rub more closely against one another with less of the shock-absorbing benefits of cartilage. The rubbing can result in pain, swelling, stiffness, decreased mobility as well as the possibility of bone spur formation. The most common cause of osteoarthritis of the knee is age. However, several factors increase the risk of developing significant arthritis including age, weight, repetitive stress injuries, and certain athletic endeavors such as soccer, tennis, or long-distance running.

In an affected knee, osteoarthritis pain is often caused by an unbalanced loading on the medial or lateral compartment of the joint. Such unbalanced loading can generate increased pressure and reduce the clearance space between the condyles of the femur and tibial plateau. Increased pressure between the femoral and tibial surfaces in an affected compartment of the knee joint can lead to cartilage degeneration. As the cartilage degenerates, the osteoarthritis sufferer experiences increased pain in the knee.

Orthopedic knee braces are commonly applied to the leg to treat osteoarthritis of the knee and other painful knee conditions. Such braces typically include an upper support portion, a lower support portion, and one or more hinge assemblies pivotally interconnecting the upper and lower support portions. The upper support portion is secured to the wearer's upper leg, while the lower support portion is secured to the wearer's lower leg. The hinge assembly is located to a side of the wearer's knee and a condyle pad is typically located between each hinge assembly and the adjacent side of the knee. For example, a thickness of the adjacent condyle pad may be increased or the pad may be moved closer to the knee. The applied force generates resultant forces in the medial/lateral plane above and below the knee. The upper and lower support portions of the brace, respectively, apply these resultant forces on the side of the affected compartment. The applied and resultant forces comprise the three-point bending load on the leg. This load realigns the knee. By realigning the orientation of the knee joint, the knee brace reduces the load in the affected compartment of the knee, thereby lessening the pain and the other negative effects of osteoarthritis.

Osteoarthritis knee braces are primarily designed to correct the abnormal bending of the knee joint inwards or outwards (i.e., Varus or Valgus correction, respectively) and prevent the "bone-on-bone" contact of the femur and tibia bones in the medial and/or lateral compartment of the knee joint as the patient bares weight during ambulation. This action of lifting the femur, pulling down the tibia or keeping the femur and tibia bones from coming in contact during the straightening of the knee during heel strike of the foot is often called "unloading" of the knee joint. By unloading the knee joint, the constant irritation of the degenerated cartilage in the effected compartment of the knee (medial or lateral) can lead to a reduction in pain and a further reduction in injury to the knee joint.

Osteoarthritis knee braces also provide improved alignment of the upper and lower aspects of the knee joint by preventing the bending inwards or outwards of the knee joint during gait. U.S. Pat. No. 3,581,741 to Rosman, discloses a knee brace comprising an upper rigid body portion and a lower rigid body portion pivotably coupled together on the lateral side in a manner so that they may pivot relative to each other about an axis generally perpendicular to the zone of overlap and may slide relative to each other in all radial directions generally parallel to the zone of overlap. A majority of knee orthotics available to treat osteoarthritis of the knee utilize a single upright attached to an upper thigh cuff and lower shin cuff. The upright is located on the side of the collapsed compartment of the knee (i.e., medial side for medial compartment osteoarthritis or lateral side for lateral compartment osteoarthritis). The attached cuffs "unload" the biomechanical force from the affected compartment of the knee by increasing the joint space on the affected side as the knee goes from flexion to extension.

Some osteoarthritis knee braces use an angled strap that extends from the upper part of the brace, from the single upright, across the opposite side of the knee joint to the lower part of the brace to improve the alignment of the knee during ambulation and more evenly balance the forces on the knee during gait kinetics. The strap provides a three point leverage system that attempts to pull the knee joint into proper alignment during gait. A combination of the single sided upright with cuff attachments and the valgus-producing strap have shown to provide improved performance in severe osteoarthritis. However, it is difficult to set the desired degrees of flexion and extension in such devices and therefore these devices are known to fall short of providing a close-to-complete alleviation of the pain and discomfort from osteoarthritis and a return to normal walking gait, let alone providing any corrective and therapeutic force system to rehabilitate the effected knee joint and surrounding muscles. Further, patient discomfort and brace slippage is a real and common problem with these prior art braces.

Some knee braces utilize a single upright support attached to an upper thigh cuff and lower shin cuff. The upright support is located opposite or adjacent to the side of the collapsed compartment of the knee. The attached cuffs "unload" the biomechanical force on the affected compartment of the knee by increasing the joint space on the affected side as the knee goes from flexion to extension. Other known brace designs employ a double upright strut, which immobilizes the knee by unloading the degenerative knee compartment. In some such braces, non-slippage and comfort pads are employed along inner lateral surfaces of the upright struts.

Patients who suffer joint pain may also benefit from the use of compression sleeves or wrap-arounds. Available compression sleeves use a flexible, elastic fabric, such as neoprene, designed to be pulled over or wrapped around the joint. Compression sleeves can improve joint stability and also provide some insulation or heat to the joint. In some instances, a compression sleeve may include one or more rods which may provide support to the joint.

There remains a need for improved osteoarthritis braces to serve the needs of the growing population of osteoarthritis sufferers. Moreover, there exists a need for a customizable osteoarthritis brace.

SUMMARY

A customizable knee brace for use in the treatment of osteoarthritis is provided. The customizable knee brace includes a lateral upright. The lateral upright includes at least a first semi-rigid support, a second semi-rigid support, and a hinge physically coupling the first semi-rigid support and the second semi-rigid support. The customizable knee brace further includes a thigh cuff constructed of formable material and coupled to the first semi-rigid support. The customizable knee brace further includes a shin cuff constructed of formable material and coupled to the second semi-rigid support. The customizable knee brace further includes an elastomeric web framework coupled to the lateral upright and configured to secure an area of a knee of a patient when wearing the customizable knee brace. The customizable knee brace further includes at least one tensioning element configured to adjust a tension of the elastomeric web framework.

Another customizable knee brace for use in the treatment of osteoarthritis is provided. The customizable knee brace includes a lateral upright. The lateral upright includes at least a first semi-rigid support, a second semi-rigid support, and a hinge physically coupling the first semi-rigid support and the second semi-rigid support. The customizable knee brace further includes an elastomeric web framework coupled to the lateral upright and configured to secure an area of a knee of a patient when wearing the customizable knee brace. The customizable knee brace further includes at least one tensioning element configured to adjust a tension of the elastomeric web framework.

Another customizable knee brace for use in the treatment of osteoarthritis is provided. The customizable knee brace includes a lateral upright. The lateral upright includes at least a first semi-rigid support, a second semi-rigid support, and a hinge physically coupling the first semi-rigid support and the second semi-rigid support. The customizable knee brace further includes a thigh cuff constructed of formable material and coupled to the first semi-rigid support. The customizable knee brace further includes a shin cuff constructed of formable material and coupled to the second semi-rigid support. The customizable knee brace further includes an elastomeric web framework coupled to the lateral upright and configured to secure an area of a knee of a patient when wearing the customizable knee brace.

A method for treating osteoarthritis utilizing a customizable knee brace is provided. The method includes forming a thigh cuff of the customizable knee brace to a thigh of a patient. The method includes forming a shin cuff of the customizable knee brace to a shin of the patient. The customizable knee brace further comprises a lateral upright comprising at least a first semi-rigid support configured to be coupled to the thigh cuff, a second semi-rigid support configured to be coupled to the shin cuff, and a hinge physically coupling the first semi-rigid support and the second semi-rigid support. The method further includes securing an area of a knee of a patient utilizing an elastomeric web framework coupled to the lateral upright. The method includes adjusting a tension of the elastomeric web framework utilizing at least one tensioning element.

A kit for providing a customizable knee brace for use in the treatment of osteoarthritis is provided. The kit includes the customizable knee brace, which includes a lateral upright including a first semi-rigid support, a second semi-rigid support, and a hinge physically coupling the first semi-rigid support and the second semi-rigid support. The customizable knee brace further includes a thigh cuff constructed of formable material and coupled to the first semi-rigid support. The customizable knee brace further includes a shin cuff constructed of formable material and coupled to the second semi-rigid support. The customizable knee brace further includes an elastomeric web framework coupled to the lateral upright and configured to secure an area of a knee of a patient when wearing the customizable knee brace. The customizable knee brace further includes at least one tensioning element configured to adjust a tension of the elastomeric web framework. The kit may further include a plurality of heating pads configurable to heat the thigh cuff and the shin cuff for forming to the patient's thigh and shin, respectively.

DETAILED DESCRIPTION OF CERTAIN EMBODIMENTS

Figure 1:
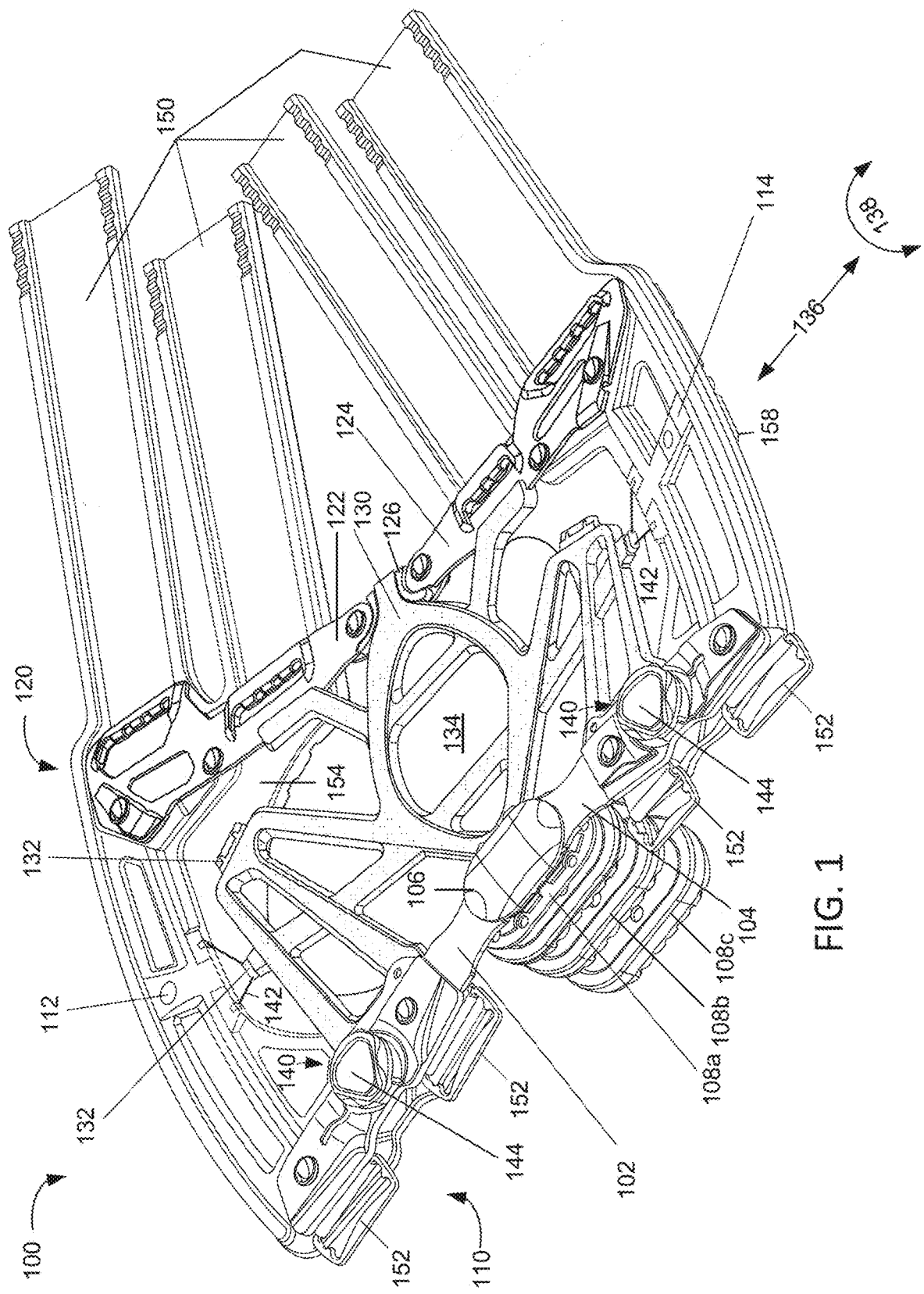
FIG. 1 illustrates a perspective view of a customizable knee brace for use in the treatment of osteoarthritis, in accordance with some embodiments.

As an initial matter, a skilled artisan will appreciate that the embodiments disclosed herein have broad application and utility. Several embodiments may be discussed for illustrative purposes in providing a full and enabling disclosure. Moreover, many adaptations, variations, modifications, and equivalent arrangements will be implicitly disclosed by the embodiments described herein and fall within the scope of this description.

Several embodiments of a customizable knee brace intended for patients with abnormal knee function who suffer from osteoarthritis (OA). As will be described in greater detail below and as illustrated in the FIGs., some embodiments of this customizable knee brace comprise a lateral upright, a thigh cuff and a shin cuff, each constructed of formable material, and an anterior elastomeric web framework configured to wrap around and conform to the patient's knee joint. The embodiments described herein benefit from, in part, the surprising development of a fully customizable, easy to wear, and light weight solution for patients suffering from OA.

Such customizable knee braces offer significant benefits over current braces. For example, customizable knee braces as described herein are a fully customizable, easy to wear, and lightweight solution for patients suffering from OA. More specifically, clinicians and patients may customize the fit of the customizable knee braces to redistribute a portion of a load from an affected compartment of the knee of the patient (e.g., medial compartment, lateral compartment, patellofemoral compartment, or any combination thereof), thereby reducing knee pain. Assisting in proper fit and effective redistribution of the load on the knee, the thigh cuff and the shin cuff are both heat formable at a relatively low heat, as will be described in greater detail in connection with at least FIGS. 1 and 9 below. A strapping system is further provided, which may be initially sized and also capable of being further trimmed as required, based at least in part on the anatomy, needs and condition of the particular patient.

Embodiments described herein provide pain relief for OA utilizing frontal-plane three-point leverage offloading with extension assist afforded by the anterior elastomeric web framework. Such three-point leverage offloading is accomplished in a plurality of manners. For example, portions of the lateral upright may be configured to be adjusted (e.g., bent or formed to an ideal or desired offloading angle with respect to the femur, tibia, knee joint, or outside surface of the upper and/or lower leg), based on anatomical needs of the patient, so as to effectively redistribute a portion of a load from an affected compartment of the knee of the patient, thereby reducing knee pain. Moreover, as will be described in more detail in connection with the following FIGS., a hinge of the lateral upright may be adjusted to increase or decrease offloading. In addition, at least one tensioning element and single spacing provided by the plurality of removable condyle pads stacked against one another may be configured to individually adjust a tension of the elastomeric web framework to thereby simultaneously increase or decrease offload from an affected compartment of the patient's knee joint while simultaneously providing varying degrees of extension assist to the knee joint and adjustment of the fit of the customizable knee brace.

Although the present embodiments are particularly well-suited for use in treating osteoarthritis of the knee, such customizable braces may also be utilized and/or modified for use in treating other joints including, for example, ankle, elbow, neck, back, and/or wrist.

FIG. 1 illustrates a perspective view of a customizable knee brace 100 for use in the treatment of osteoarthritis, in accordance with some embodiments. Customizable knee brace 100 is illustrated in FIG. 1 before fitting to a patient's knee, in a substantially flat orientation. Customizable knee brace 100 comprises a lateral upright 110, which comprises a first semi-rigid support 102, a second semi-rigid support 104, and a hinge 106 physically coupling first semi-rigid support 102 and second semi-rigid support 104. In some embodiments, hinge 106 may be a unicentric joint (e.g., having a single axis of rotation or freedom of movement). In some other embodiments, hinge 106 may be a polycentric joint (e.g., having a plurality of axes of rotation or freedom of movement). In some embodiments, at least one of first semi-rigid support 102 and second semi-rigid support 104 are configured to be adjusted, based on anatomical needs of the patient, so as to redistribute a portion of a load from an affected compartment of the knee of the patient, thereby reducing knee pain. For example, a treating clinician or the patient may bend or form one or both of first semi-rigid support 102 and second semi-rigid support 104 such that it forms an ideal or desired offloading angle with respect to the femur, tibia, knee joint, or external surface of the upper and/or lower leg of the patient when the customizable knee brace 100 is properly worn. Accordingly, in some embodiments, first semi-rigid support 102 and second semi-rigid support 104 may be constructed of a material such as heat-formable plastic, metal, or any other suitably rigid material, currently know or unknown, that is sufficiently rigid to provide the required support to and force against the knee joint and that, in some embodiments, may also be adjusted or bent to a desired angle either through use of an adjusting machine or manually, by hand, and in some embodiments, once sufficiently heated.

For treatment of medial compartment OA, lateral upright 110 may be disposed along the lateral side of the patient's affected leg such that hinge 106 substantially aligns with the lateral side of the knee joint and the axis along which the knee bends, first semi-rigid support 102 is disposed along the lateral, lower portion of the patients upper leg (e.g., the thigh), and second semi-rigid support 104 is disposed along the lateral, upper portion of the patients lower leg (e.g., the shin and/or calf). Accordingly, when worn, the lateral upright 110 (e.g., first semi-rigid support 102, hinge 106, and/or second semi-rigid support 104) may exert a force from the lateral side toward the medial side of the knee joint (i.e., a Varus adjustment), thereby increasing the separation between the femur and tibia in the medial compartment of the knee and, accordingly, providing a redistribution of a portion of the load away from the medial compartment of the knee. In at least this manner, knee pain may be reduced for the patient suffering from medial OA.

For treatment of lateral compartment OA, lateral upright 110 may be disposed along the medial side of the patient's affected leg such that hinge 106 substantially aligns with the medial side of the knee joint and the axis along which the knee bends, first semi-rigid support 102 is disposed along the medial, lower portion of the patients upper leg (e.g., the thigh), and second semi-rigid support 104 is disposed along the medial, upper portion of the patients lower leg (e.g., the shin and/or calf). Accordingly, when worn, the lateral upright 110 (e.g., first semi-rigid support 102, hinge 106, and/or second semi-rigid support 104) may exert a force from the medial side toward the lateral side of the knee joint (i.e., a Valgus adjustment), thereby increasing the separation between the femur and tibia in the lateral compartment of the knee and, accordingly, providing a redistribution of a portion of the load away from the lateral compartment of the knee. In at least this manner, knee pain may be reduced for the patient suffering from lateral OA.

In some embodiments, customizable knee brace 100 may further comprise at least one removable condyle pad 108a, 108b, 108c coupled to hinge 106, between hinge 106 and the knee of the patient, thereby providing a desired spacing between hinge 106 and the knee of the patient. In some embodiments, removable condyle pad(s) 108a, 108b, 108c may be secured to hinge 106 via Velcro, a removable or permanent adhesive, one or more mounting brackets, screws, clips or any other suitable method of coupling. Moreover, a single removable condyle pads 108a, 108b, 108c may be utilized at a time, or multiple removable condyle pads 108a, 108b, 108c may be stacked to provide a desired spacing between hinge 106 and the patient's knee. By coupling one or more of a plurality of removable condyle pads 108a, 108b, 108c to hinge 106, each having a different thickness, the alignment of the knee may be further adjusted, in some instances, with a finer granularity and greater range of thicknesses than would otherwise be possible.

Customizable knee brace 100 may further comprise a thigh cuff 112 coupled to first semi-rigid support 102. In some embodiments, thigh cuff 112 may be constructed of heat-formable material allowing it to be adjusted, bent and/or shaped to conform to at least the anterior portion of the patient's thigh by applying modest heat (e.g., in a temperature range at least partially overlapping 160-180 degrees Fahrenheit) and, thereby, improve the fit to the patient. In some embodiments, this heat-formable material may be substantially rigid at temperatures it would be expected to endure while being worn by the patient (e.g., temperature ranges below 120 degrees Fahrenheit). In some other embodiments, thigh cuff 112 may comprise a formable metal. In this way, thigh cuff 112 may be thermoformable, adjustable, and/or reformable such that a clinician and/or the patient may mold the brace directly to the patient for an improved fit, comfort, and joint stabilization in a desired orientation. Thigh cuff 112 may have the additional benefit of providing some measure of local tissue compression as well as promoting desired patellar and/or general knee joint alignment, either of which may provide reduced inflammation and/or pain in the knee joint. In addition, in some embodiments, thigh cuff 112 may also be light weight, easy to clean, and/or waterproof.

Customizable knee brace 100 may further comprise a shin cuff 114 coupled to second semi-rigid support 104. In some embodiments, shin cuff 114 is constructed of heat-formable material allowing it to be adjusted, bent and/or shaped to conform to at least the anterior portion of the patient's thigh by applying modest heat (e.g., in a temperature range at least partially overlapping 160-180 degrees Fahrenheit) and, thereby, improve the fit to the patient. In some embodiments, this heat-formable material may be substantially rigid at temperatures it would be expected to endure while being worn by the patient (e.g., temperature ranges below 120 degrees Fahrenheit). In some other embodiments, shin cuff 114 may comprise a formable metal. In this way, shin cuff 114 may be thermoformable, adjustable, and/or reformable such that a clinician and/or the patient may mold the brace directly to the patient for an improved fit, comfort, and joint stabilization in a desired orientation. Shin cuff 114 may have the additional benefit of providing some measure of local tissue compression as well as promoting desired patellar and/or general knee joint alignment, either of which may provide reduced inflammation and/or pain in the knee joint. In addition, in some embodiments, shin cuff 114 may also be light weight, easy to clean, and/or waterproof.

Customizable knee brace 100 may further comprise a medial element 120, which comprises a first support 122, a second support 124, and a hinge 126 physically coupling first support 122 and second support 124. In some embodiments, first support 122 may be coupled to thigh cuff 112 and second support 124 may be coupled to shin cuff 114. In this way, medial element 120 may provide support for both the brace and the patient's knee on the side of the knee opposite lateral upright 110. In some embodiments, first support 122 and second support 124 may be constructed of a material such as plastic, metal or any other suitable material, currently known or unknown, that may provide suitable strength to adequately support the patient's knee as well as customizable knee brace 100 itself.

For treatment of medial compartment OA, medial element 120 may be disposed along the medial side of the patient's affected leg such that hinge 126 substantially aligns with the medial side of the knee joint and the axis along which the knee bends, first support 122 is disposed along the medial, lower portion of the patients upper leg (e.g., the thigh), and second support 124 is disposed along the medial, upper portion of the patients lower leg (e.g., the shin and/or calf).

For treatment of lateral compartment OA, medial element 120 may be disposed along the lateral side of the patient's affected leg such that hinge 126 substantially aligns with the lateral side of the knee joint and the axis along which the knee bends, first support 122 is disposed along the lateral, lower portion of the patients upper leg (e.g., the thigh), and second support 124 is disposed along the lateral, upper portion of the patients lower leg (e.g., the shin and/or calf).

Customizable knee brace 100 may further comprise an elastomeric web framework 130 coupled to at least one of lateral upright 110, thigh cuff 112, shin cuff 114 and medial element 120. Elastomeric web framework 130 may comprise a plurality of interconnected elastomeric segments 132 that define a plurality of permanent openings, at least one of which includes an alignment opening 134 configured to receive a patellar portion of the knee of the patient when customizable knee brace 100 is properly worn. In some embodiments, at least segments of the plurality of interconnected elastomeric segments 132 that define alignment opening 134 may have a substantially similar thickness and cross-section to one another and, preferably, have a non-planar cross section (e.g., the cross-sections of those segments comprise at least one edge that is not prescribed by a straight line). Elastomeric web framework 130 is elastically stretchable and provides a light-weight, comfortable, secure fitting that supports correct knee alignment utilizing three points of leverage during gait. In some embodiments, elastomeric web framework 130 may comprise silicone, however, the present application is not so limited, and elastomeric web framework 130 may comprise any suitably stretchable and flexible material. Moreover, the web-like framework provides a breathable, stable, yet flexible brace that may not otherwise be possible even utilizing similar materials but not the web-like structure. In some embodiments, at least portions of a surface of elastomeric framework 130 may comprise texturing elements to promote increased gripping and reduced slippage when customizable knee brace 100 is worn.

When properly worn, elastomeric web framework 130 may be tensioned utilizing at least one tensioning element 140, as will be described in more detail below, and extends in both a first, axial direction 136 and a second, circumferential direction 138 such that it abuts at least the lower thigh, knee, and upper shin as is disclosed in U.S. Patent Pub. No. U.S. 2006/0030804, the contents of which are incorporated by reference in their entirety. Such tensioning allows customizable knee brace 100 as a whole, and elastomeric web framework 130 in particular, to conform to the patient's knee, thereby absorbing physical shock and returning kinetic energy while ambulating in addition to providing increased stability and integrity of customizable knee brace 100 by virtue of the connection with at least one of lateral upright 110, thigh cuff 112, shin cuff 114, and medial element 120. Moreover, elastomeric web framework 130 is configured to disperse energy across the knee and can additionally address patellofemoral pain associated with OA at least by securing and tracking an area of a knee of a patient (e.g., the patella), while both customizing a fit of the brace around the knee of the patient and redistributing at least a portion of a load from a desired compartment of the knee of the patient (e.g., one or more of the medial, lateral, and patellofemoral compartments) when wearing the customizable knee brace. In some embodiments, tensioning elastomeric web framework 130 may increase offloading of a portion of a load on a desired compartment of the knee (e.g., the medial or lateral compartment) while also increasing an amount of vertical tension in elastomeric web framework 130.

At least one tensioning element 140 is configured to adjust a tension of elastomeric web framework 130. In some implementations, tensioning element(s) 140 may be disposed on lateral upright 110 (e.g., on one or both of first semi-rigid support 102 and second semi-rigid support 104). However, the present application is not so limited and tensioning element(s) 140 may be disposed at any suitable location on customizable knee brace 100. FIG. 1 illustrates a reel-and-lace tensioning element, which comprises a lace 142 coupled to elastomeric web framework 130 and at least one reel element 144 configure to adjust a tension in lace 142, thereby adjusting the tension in elastomeric web framework 130. Tensioning element(s) 140 are described in more detail in connection with at least FIGS. 2 and 3. Tensioning element(s) 140 are configured to provide for micro-adjustment of the tension applied to elastomeric web framework 130, which not only allows adjustment of the offloading of a portion of a load from a desired compartment of the knee of the patient, but also simultaneously improves the fit of elastomeric web framework 130 against the surface of the patient's knee and preventing gapping and reducing pooching of the web. In this way, tensioning element(s) 140 maintains desired tension across substantially the entirety of elastomeric web framework 130, from thigh cuff 112 to shin cuff 114 and from lateral upright 110 to medial element 120.

Although FIG. 1 illustrates a reel-and-lace tensioning element, the present application is not so limited, and tensioning element(s) 140 may also, or alternatively, comprise any of a lever-based tensioning element, a screw-based tensioning element, a lace-and-cleat tensioning element, similar to those utilized on sail boats, buckles, a rigid post-and-strap tensioning element with belt-type holes, a hook-and-loop (e.g., Velcro®) tensioning element, a notched band-and-pawl tensioning element, similar to those utilized on ski boots, or any other apparatus configured to adjust a tension in another element.

Customizable knee brace 100 may additionally comprise at least one strap 150 configured to wrap around at least a posterior portion of the patient's knee thereby securing the brace to the patient. In some embodiments, strap(s) 150 may be physically coupled to medial element 120 and may be configured to couple to respective fastening element(s) 152, which are configured to receive strap(s) 150 and are coupled to lateral upright 110 (as shown in FIG. 1). In some other embodiments, strap(s) 150 may be physically coupled to lateral upright 110 and may be configured to couple to respective fastening element(s) 152 coupled to medial element 120 (opposite of that shown in FIG. 1). Strap(s) 150 may be sized appropriately for the requirements of the patient and of the customizable knee brace 100. In some embodiments, strap(s) 150 may be further trimmed by a clinician and/or the patient in accordance with the requirements of the patient and of the customizable knee brace 100. Further, in some embodiments, strap(s) 150 may be removable for hygienic cleansing or for any other desired purpose.

Customizable knee brace 100 may additionally comprise a thigh pad 154 configured to provide cushioning to the patient's thigh. In some embodiments, thigh pad 154 may be formable, preferably heat-formable, may comprise foam, fabric, rubber, or any other cushioning material, and may promote improved comfort and fit of customizable knee brace 100. In some embodiments, thigh pad 154 may be physically coupled to and removable from at least thigh cuff 112 and, in some embodiments, may also be coupled to and removable from either or both of lateral upright 110 and medial element 120.

Customizable knee brace 100 may additionally comprise a calf pad 158 configured to provide cushioning to the patient's calf. In some embodiments, calf pad 158 may be formable, preferably heat-formable, may comprise foam, fabric, rubber, or any other cushioning material, and may promote improved comfort and fit of customizable knee brace 100. In some embodiments, calf pad 158 may be physically coupled to and removable from at least shin cuff 114 and, in some embodiments, may also be coupled to and removable from either or both of lateral upright 110 and medial element 120. Although shown as separate, in some embodiments, thigh pad 154 and calf pad 158 may comprise a unitary member configured to provide cushioning to both the patient's posterior thigh and calf.

In some embodiments, customizable knee brace 100 may further comprise a removable wearable sleeve (not shown in FIG. 1) configured to be worn over the knee joint and under the remainder of customizable knee brace 100. In some embodiments, the wearable sleeve may comprise a lightweight, stretchy and breathable material that provides some degree of compression to the patient's knee joint.

Through the combined operation of any combination of lateral upright 110, medial element 120, thigh cuff 112, shin cuff 114, elastomeric web framework 130, tensioning element(s) 140, strap(s) 150, thigh pad 154, and/or shin pad 158, medial-lateral and rotation control, with or without Varus/Valgus adjustment, may be customized to fit a specific patient.

Figure 2:
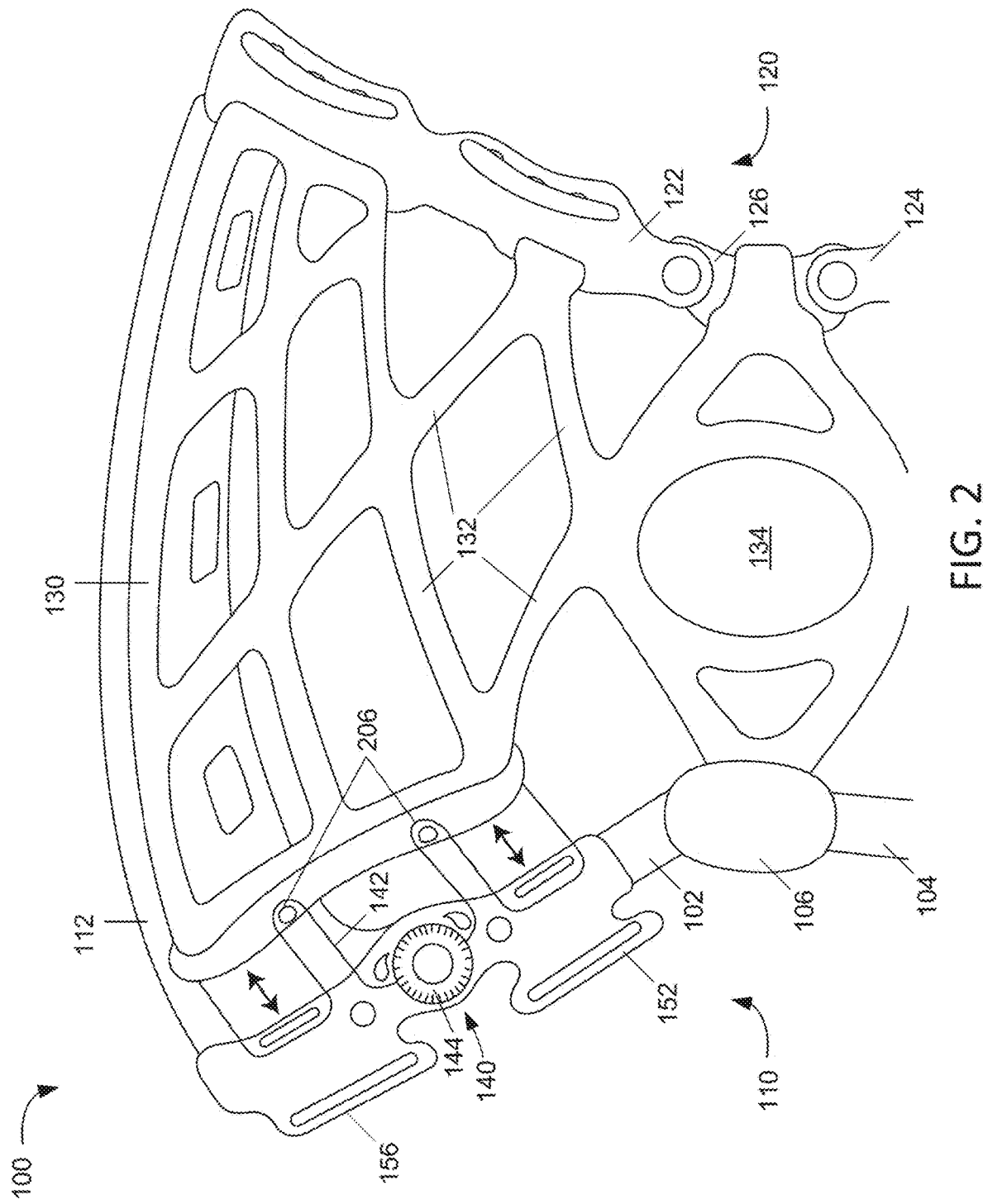
FIG. 2 illustrates a plan view of an embodiment of an upper portion of the customizable knee brace of FIG. 1, utilizing a reel-and-lace tensioning element, in accordance with some embodiments.

FIG. 2 illustrates a plan view of an embodiment of an upper portion of customizable knee brace 100 of FIG. 1, utilizing a reel-and-lace tensioning element, in accordance with some embodiments. FIG. 2 illustrates lateral upright 110, comprising first semi-rigid support 102, second semi-rigid support 104 and hinge 106, thigh cuff 112, shin cuff 114, medial element 120, comprising first support 122, second support 124 and hinge 126, elastomeric web framework 130, comprising the plurality of interconnected elastomeric segments 132 defining alignment opening 134, and tensioning element 140, comprising lace 142 (not shown in FIG. 2) and reel element 144, as previously described in connection with FIG. 1. FIG. 2 illustrates an embodiment where elastomeric web framework 130 at least partially overlaps thigh cuff 112. In addition, FIG. 2 illustrates tensioning element 140 as a reel-and-lace tensioning element, comprising lace 142 coupled to elastomeric web framework 130 and reel element 144 configured to adjust a tension in lace 142, thereby adjusting the tension in elastomeric web framework 130. As shown in FIG. 2, lace 142 may be anchored at one or both ends to elastomeric web framework 130. However, lace 142 may also be anchored at one or both ends to lateral upright 110, for example, to first semi-rigid upright 102. Lace 142 may be threaded between elastomeric web framework 130 and lateral upright 110 one or more times, passing through guides 206 coupled to one or both of elastomeric web framework 130 and lateral upright 110, which allow lace 142 to slide freely along guides 206 as lace 142 is tensioned. In operation, rotating reel element 144 causes lace 142 to move such that elastomeric web framework 130 moves toward or away from lateral upright 110, and adjusting the tension in elastomeric web framework 130. In some embodiments, reel-and-lace tensioning element 140 may comprise an integrated dial or reel system such as the Boa closure systems developed by Boa Technologies, Inc.

Although FIG. 2 illustrates lace 142 anchored at one or both ends to elastomeric web framework 130, the present application is not so limited and lace 142 may be anchored at one or both ends of one or more of lateral upright 110, thigh cuff 112, shin cuff 114 (not shown in FIG. 2), medial element 120 and elastomeric web framework 130. In such embodiments, lace 142 may be threaded between elastomeric web framework 130 and at least one of lateral upright 110, thigh cuff 112, shin cuff 114 (not shown in FIG. 2) and/or medial element 120 one or more times, passing through guides 206 coupled to one or more of elastomeric web framework 130, lateral upright 110, thigh cuff 112, shin cuff 114, and/or medial element 120 (not shown in FIG. 2), which allow lace 142 to slide freely along guides 206 as lace 142 is tensioned.

Figure 3:
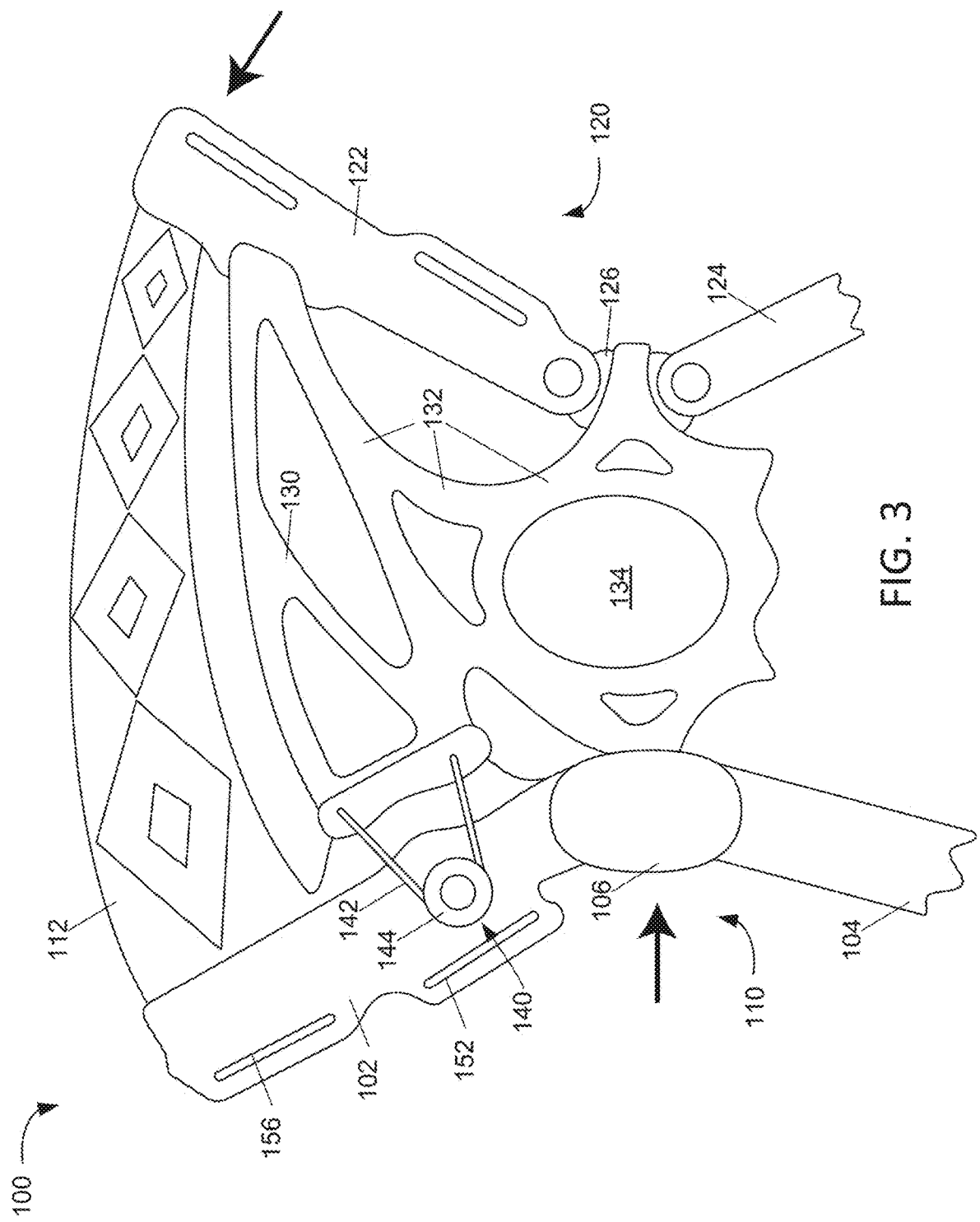
FIG. 3 illustrates a plan view of another embodiment of an upper portion of the customizable knee brace of FIG. 1, utilizing a reel-and-lace tensioning element, in accordance with some embodiments.

FIG. 3 illustrates a plan view of another embodiment of an upper portion of customizable knee brace 100 of FIG. 1, utilizing a reel-and-lace tensioning element, in accordance with some embodiments. FIG. 3 illustrates each aspect previously described in connection with FIG. 2, however, illustrating elastomeric web framework 130 as being disposed adjacent to, but not overlapping, thigh cuff 112.

Figure 4:
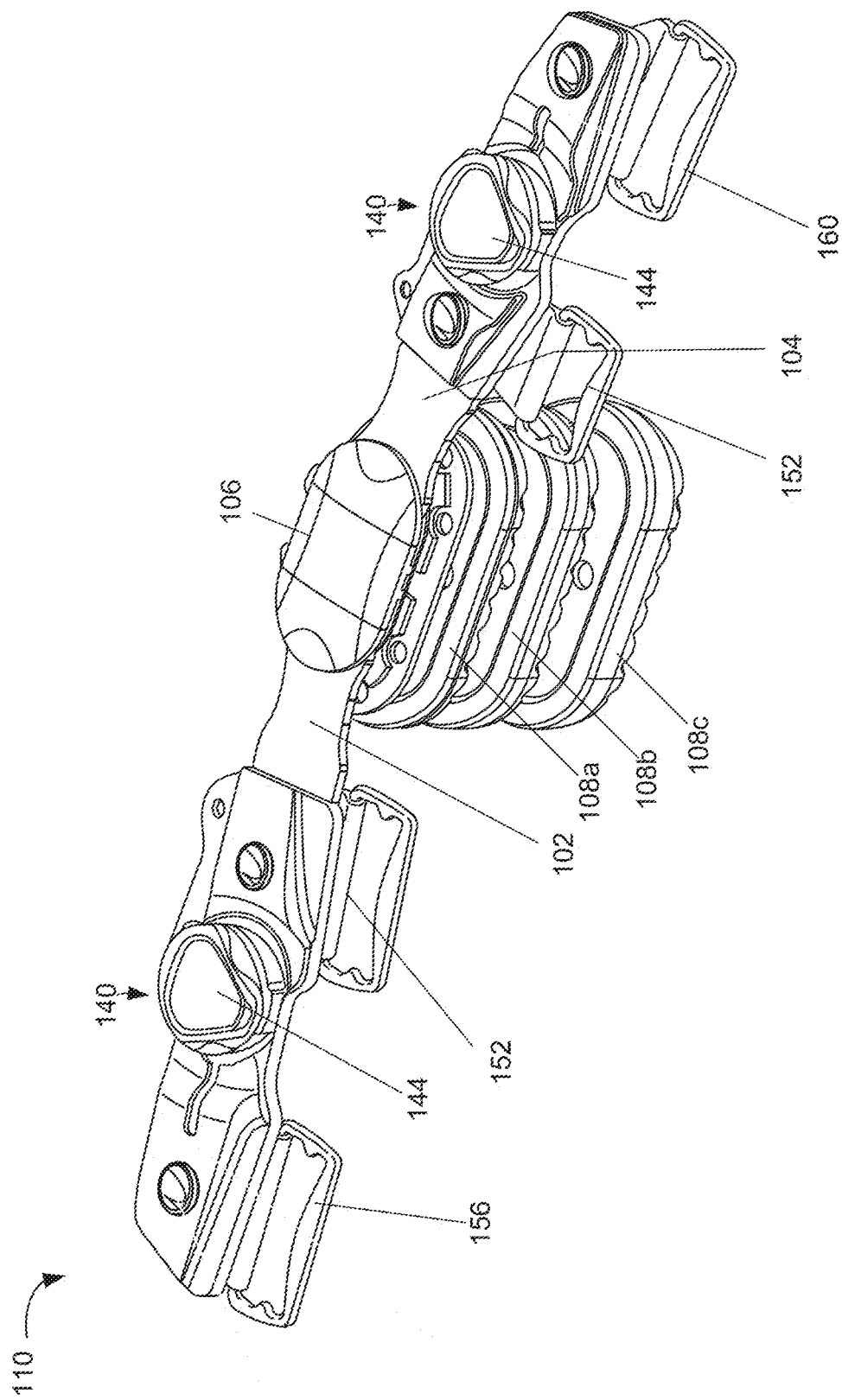
FIG. 4 illustrates a perspective, magnified view of the lateral upright of customizable knee brace of FIG. 1, in accordance with some embodiments.

FIG. 4 illustrates a perspective, magnified view of lateral upright 110 of customizable knee brace 100 of FIG. 1, in accordance with some embodiments. FIG. 4 illustrates first semi-rigid support 102, second semi-rigid support 104, hinge 106, tensioning elements 140 and fastening elements 152, as previously described in connection with FIG. 1. Compared to FIG. 1, FIG. 4 shows a larger view with more detail for each of these elements.

Figure 5:
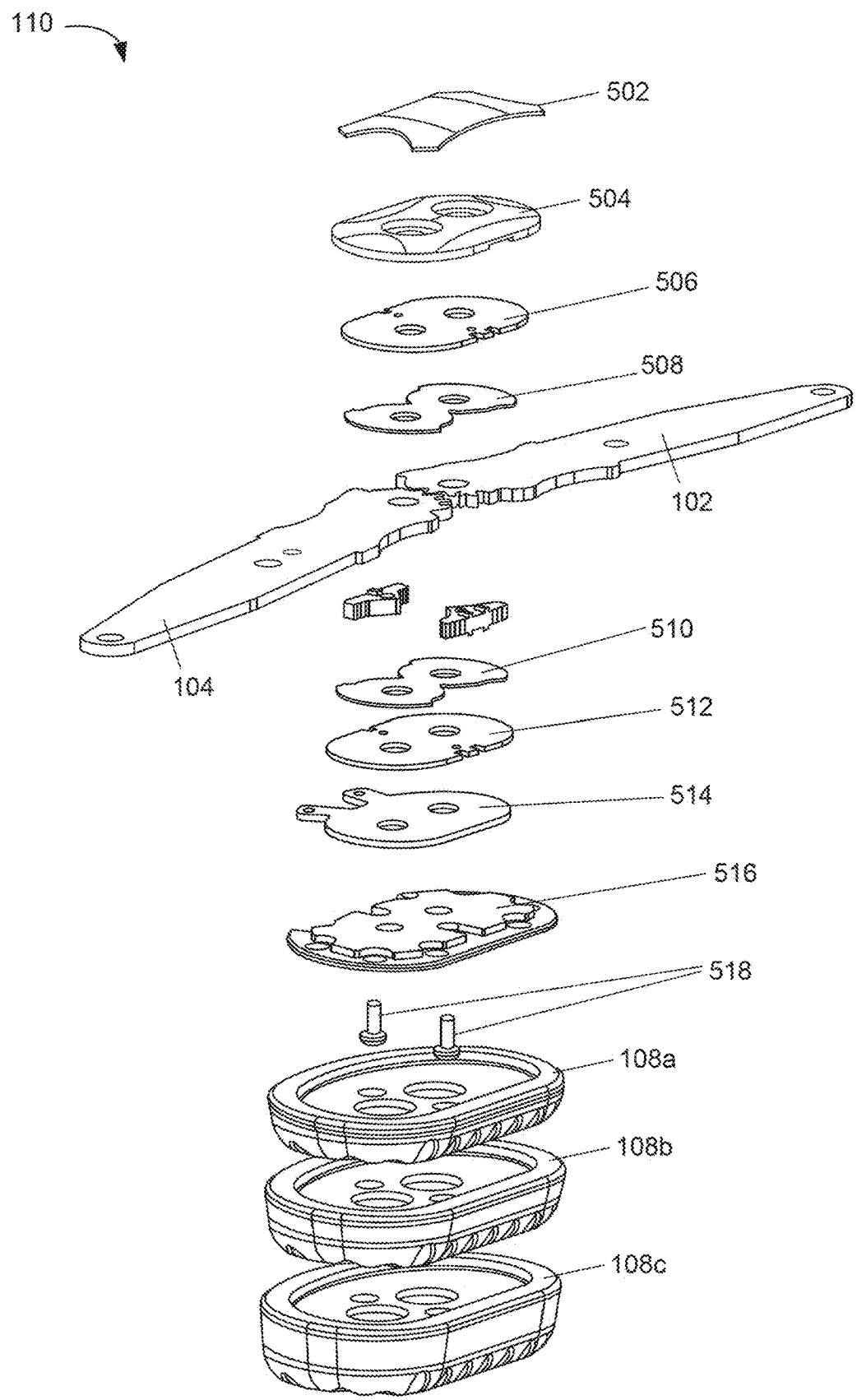
FIG. 5 illustrates an exploded perspective view of the lateral upright of FIGS. 1 and 4, in accordance with some embodiments.

FIG. 5 illustrates an exploded perspective view of lateral upright 110 of FIGS. 1 and 4, in accordance with some embodiments. Although several additional elements of lateral upright 110 are described in connection with FIG. 5, all, a subset of all, or none, of these additional elements may be required for proper operation depending on the specific embodiment.

FIG. 5 illustrates a logo plate 502, a hinge bezel 504, an unthreaded hinge plate 506, and a first low friction washer 508 disposed on an outside (e.g., lateral side) of first semi-rigid support 102 and second semi-rigid support 104 of lateral upright 110. FIG. 5 further illustrates a second low friction washer 510, a threaded hinge plate 512, plastic threaded hinge plate 514, and a condyle plate 516 on an inside (e.g., medial side) of first semi-rigid support 102 and second semi-rigid support 104 of lateral upright 110. Each of hinge bezel 504, unthreaded hinge plate 506, first low friction washer 508, first semi-rigid support 102, second semi-rigid support 104, second low friction washer 510, threaded hinge plate 512, plastic threaded hinge plate 514, and condyle plate 516 may comprise holes to receive screws 518, which are configured to secure the elements of lateral upright 110 together into a functional, integrated unit. FIG. 5 further illustrates removable condyle pads 108a, 108b, 108c, as previously described in connection with FIG. 1.

Figure 6:
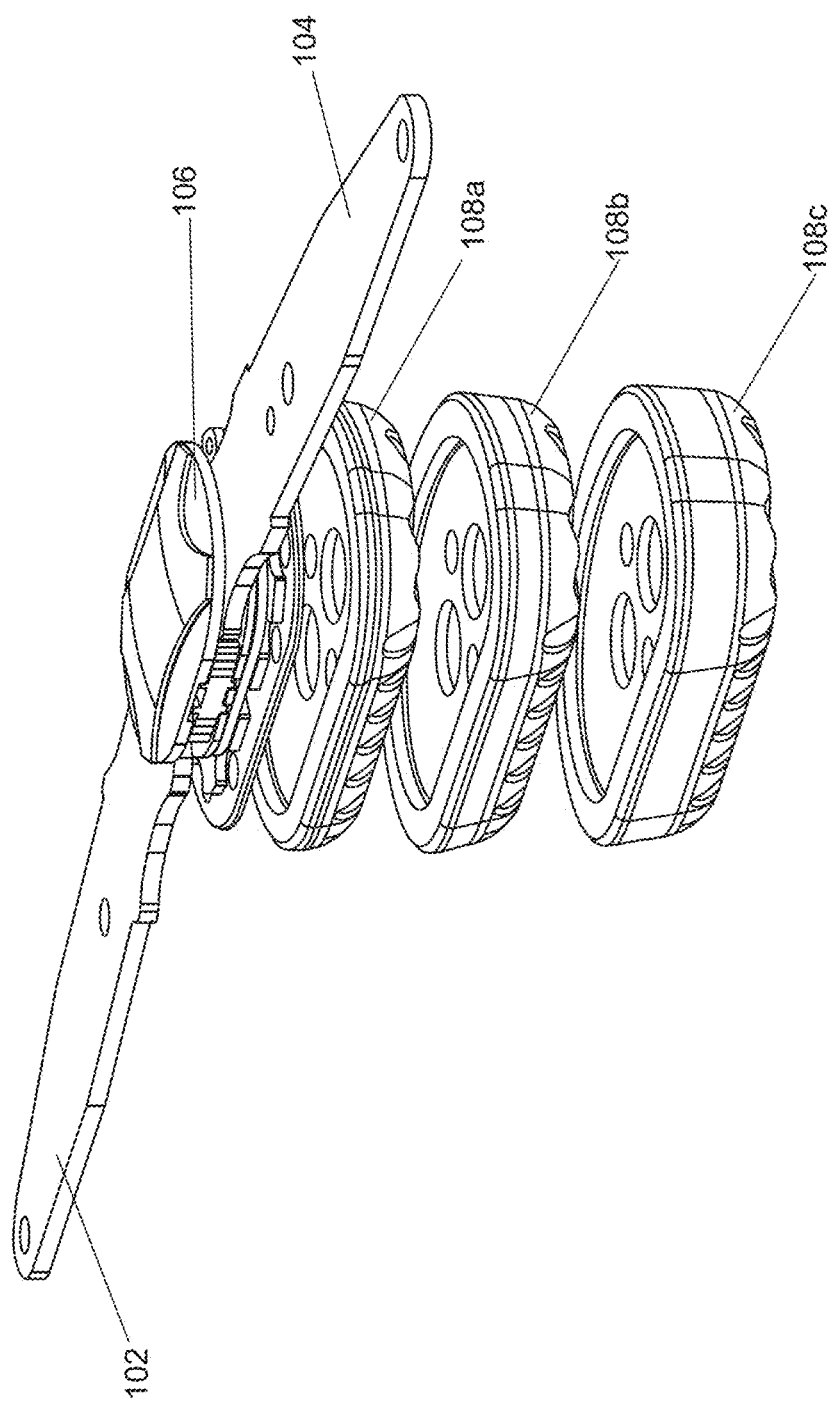
FIG. 6 illustrates an exploded perspective view of the removable condyle pads for coupling to the lateral upright of FIGS. 1, 4 and 5, in accordance with some embodiments.

FIG. 6 illustrates an exploded perspective view of removable condyle pads 108a, 108b, 108c for coupling to lateral upright 100 of FIGS. 1, 4 and 5, in accordance with some embodiments. FIG. 6 illustrates first semi-rigid support 102, second semi-rigid support 104, hinge 106, and removable condyle pads 108a, 108b, 108c, as previously described in connection with FIG. 1. In some embodiments, each of removable condyle pads 108a, 108b, 108c may have a different thickness. Accordingly, a clinician and/or patient may select one of removable condyle pads 108a, 108b, 108c for coupling to hinge 106 in order to provide a desired spacing between hinge 106 and the knee of the patient. In some other embodiments, a combination of removable condyle pads 108a, 108b, 108c may be utilized simultaneously in order to provide a greater selection and greater range of spacings between hinge 106 and the knee of the patient as compared to selecting only one of removable condyle pads 108a, 108b, 108c.

Figure 7:
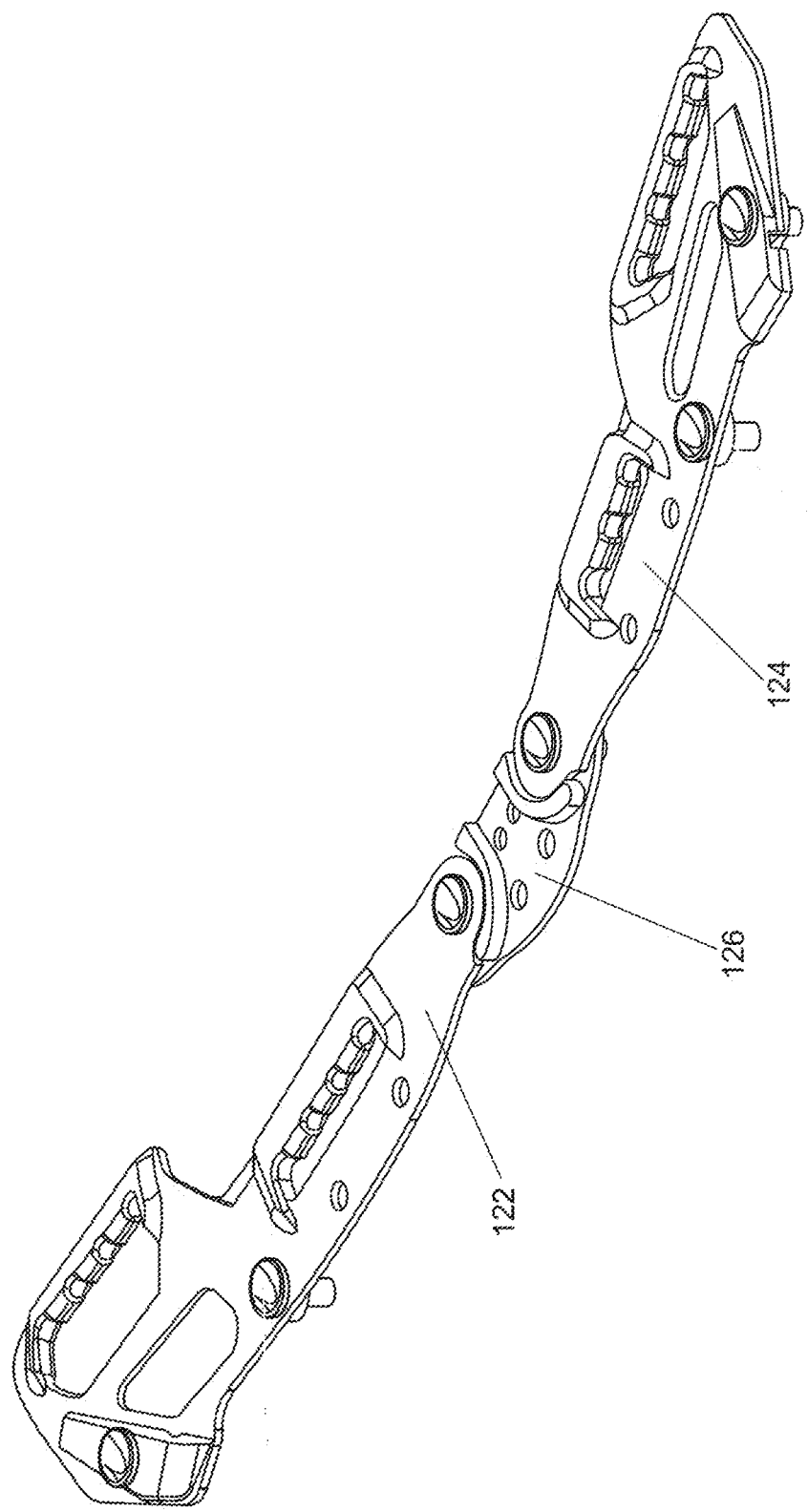
FIG. 7 illustrates a perspective view of the medial element of the customizable knee brace of FIG. 1, in accordance with some embodiments.

FIG. 7 illustrates a perspective view of medial element 120 of customizable knee brace 100 of FIG. 1, in accordance with some embodiments. FIG. 7 illustrates first support 122, second support 124, and hinge 126, as previously described in connection with FIG. 1. Compared to FIG. 1, FIG. 7 merely shows a larger view with more detail for each of these elements.

Figure 8:
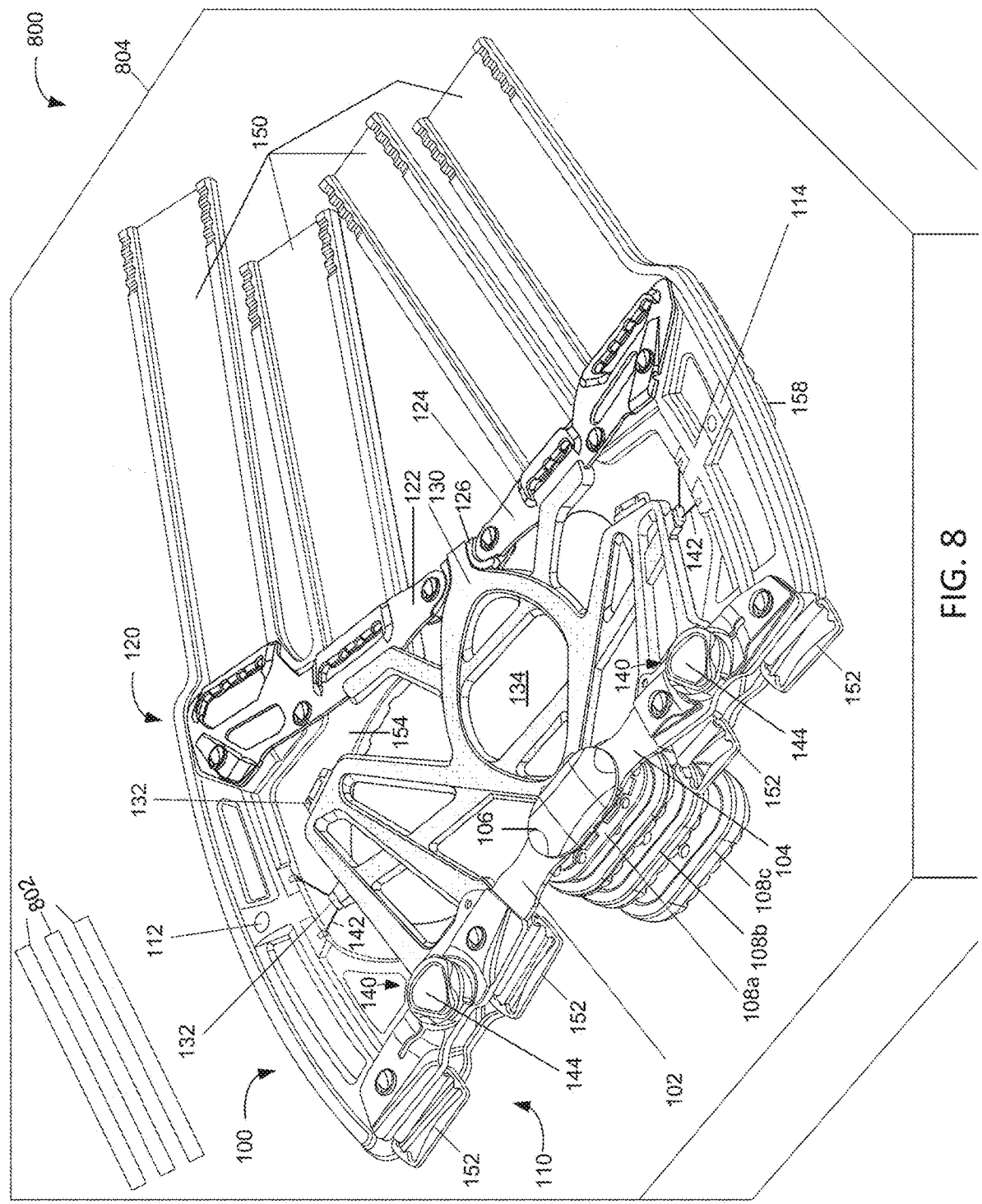
FIG. 8 illustrates a kit for reducing or substantially eliminating deformation of elements of the customizable knee brace of FIG. 1 during physical transportation and/or storage, in accordance with some embodiments.

FIG. 8 illustrates a kit 800 for reducing or substantially eliminating deformation of elements of the customizable knee brace of FIG. 1 during physical transportation and/or storage, in accordance with some embodiments. In some embodiments, kit 800 may comprise each element or a subset of the elements of customizable knee brace 100, as previously described in connection with FIG. 1. In some embodiments, customizable knee brace 100 may be assembled in kit 800. In some other embodiments, customizable knee brace 100 may be unassembled as its constituent elements in kit 800. In some embodiments, kit 800 may further comprise a plurality of heating pads 802 configured to be applied directly to thigh cuff 112 and/or shin cuff 114 to heat them into a temperature range within which they become formable, as previously described, such that a clinician and/or the patient may conform thigh cuff 112 and shin cuff 114 to the patient's thigh and calf for a customized fit. In some embodiments, heating pads 802 may further comprise a surface having an adhesive thereon such that heating pads 802 may be adhered for heating the respective element of customizable knee brace 100. In some embodiments, kit 800 may further comprise packaging 804 configured to reduce or substantially eliminate alteration of a shape of any portion of customizable knee brace 100 during transit or storage within kit 800. In some embodiments, packaging 804 may comprise a plurality of foam inserts defining spaces within which at least respective portions of customizable knee brace 100 (e.g., thigh cuff 112 and shin cuff 114) may be inserted such that the general shape of customizable knee brace 100 is maintained during transport and/or storage.

Figure 9:
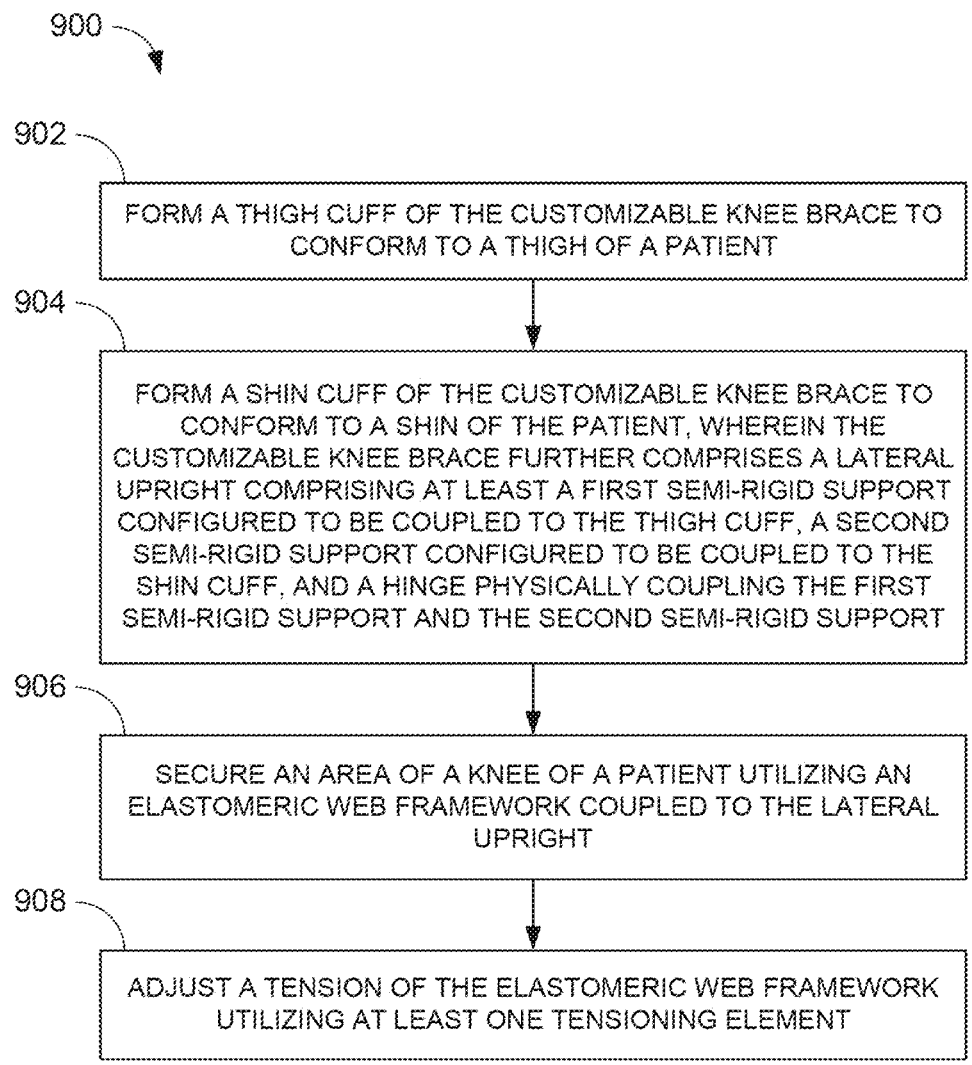
FIG. 9 illustrates a flowchart for a method of treatment of osteoarthritis utilizing a customizable knee brace as described in any of the preceding FIGS., in accordance with some embodiments.

FIG. 9 illustrates a flowchart 900 for a method of treatment of osteoarthritis utilizing a customizable knee brace as described in any of the preceding FIGs., in accordance with some embodiments. Although particular steps are described herein, the present application is not so limited and alternative methods of treatment of OA utilizing a customizable knee brace may include a subset of these steps, in the same or different order, and may additionally include one or more addition steps not described herein.

Flowchart 900 may include step 902, which includes forming a thigh cuff of the customizable knee brace to conform to a thigh of a patient. For example, as previously described in connection with at least FIG. 1, thigh cuff 112 may be heat-formed to conform to the patient's thigh in a temperature range that at least partially overlaps 160-180 degrees Fahrenheit, or comprise a formable metal.

Flowchart 900 may include step 904, which includes forming a shin cuff of the customizable knee brace to conform to a shin of the patient. For example, as previously described in connection with at least FIG. 1, shin cuff 114 may be heat-formed to conform to the patient's shin in a temperature range that at least partially overlaps 160-180 degrees Fahrenheit, or comprise a formable metal. In some embodiments, as previously described in connection with at least FIG. 1, customizable knee brace 100 may further comprise lateral upright 110, which comprises at least first semi-rigid support 102 configured to be coupled to thigh cuff 112, second semi-rigid support 104 configured to be coupled to shin cuff 114, and hinge 106 physically coupling first semi-rigid support 102 and second semi-rigid support 104.

Flowchart 900 may include step 906, which includes securing an area of a knee of a patient utilizing an elastomeric web framework coupled to the lateral upright. For example, as previously described in connection with at least FIG. 1, the patella of the patient may be secured utilizing alignment opening 134 of elastomeric web framework 130, which may be coupled to lateral upright 110.

Flowchart 900 may include step 908, which includes adjusting a tension of the elastomeric web framework utilizing at least one tensioning element. For example, as previously described in connection with at least FIGS. 1-3, tension in elastomeric web framework 130 may be adjusted individually and collectively by utilizing tension element(s) 140 by utilizing the reel to adjust a tension in the lace, which is coupled to the elastomeric web framework and extends anterior of the first semi-rigid support and between the first semi-rigid support and the elastomeric web framework, and utilizing each of the plurality of removable condyle pads by stacking the plurality of removable condyle pads against one another and coupling the plurality of removable condyle pads to the hinge. Adjusting the tension of elastomeric web framework 130 individually and collectively redistributes at least a portion of a load from a medial compartment (or from a lateral compartment) of the patient's knee. In some embodiments, adjusting the tension of elastomeric web framework 130 comprises increasing an amount of vertical tension of the elastomeric web framework 130 while simultaneously increasing an offloading of a portion of a load on a desired compartment of the knee (e.g., the medial or lateral compartments) and provides a desired degree of extension assist to the knee.

As previously described in connection with at least FIGS. 1 and 2, tensioning element(s) may comprise at least one reel element 144 and lace 142 that physically couples elastomeric web framework 130 to lateral upright 110. In such embodiments, adjusting the tension of elastomeric web framework 130 may comprise adjusting the at least one reel element 144 to adjust a tension in lace 142.

In some embodiments, flowchart 900 may further include bending at least one of the first semi-rigid support and the second semi-rigid support to a desired angle based at least in part on an alignment of the knee so as to redistribute a portion of a load from a medial compartment of the knee of the patient. For example, as previously described in connection with at least FIG. 1, one or both of first semi-rigid support 102 and second semi-rigid support 104 may be adjusted or bent to a desired angle based at least in part on an alignment of the patient's knee so as to redistribute a portion of a load from a medial compartment (or from a lateral compartment) of the patient's knee.

In some embodiments, flowchart 900 may further include disposing at least one removable condyle pad between the hinge and the knee of the patient, thereby providing a desired spacing between the hinge and the knee of the patient. For example, as previously described in connection with at least FIGS. 1 and 4-6, removable condyle pads 108a, 108b, 108c may each have different thicknesses and may be coupled between hinge 106 and the patient's knee, thereby providing a desired spacing between hinge 106 and the patient's knee.

In some embodiments, flowchart 900 may further include wrapping at least one strap, coupled to the lateral upright, around at least a posterior portion of the knee of the patient thereby securing the brace to the patient. For example, as previously described in connection with at least FIG. 1, strap(s) 150, which may be coupled to lateral upright 110 and/or medial element 120, may be wrapped around at least a posterior portion of the patient's knee, thereby securing customizable knee brace 100 to the patient.

In some embodiments, flowchart 900 may further include disposing a formable pad at the knee of the patient. For example, as previously described in connection with at least FIG. 1, one or both of thigh pad 154 and shin pad 158 may be disposed at, over, or on the patient's thigh and/or shin.

While certain embodiments are described herein in detail, it is to be understood that this disclosure is illustrative and exemplary, and is made merely for the purposes of providing a full and enabling disclosure. The detailed disclosure herein of one or more embodiments is not intended, nor is to be construed, to limit the scope of patent protection, for which scope is to be defined by the claims and the equivalents thereof. It is not intended that the scope of patent protection be defined by reading into any claim a limitation found herein that does not explicitly appear in the claim itself.

What is claimed is:

1. A customizable knee brace for use in treatment of osteoarthritis, comprising: a lateral upright comprising: a first semi-rigid support, a second semi-rigid support, and a hinge physically coupling the first semi-rigid support and the second semi-rigid support; a thigh cuff coupled to the first semi-rigid support; a shin cuff coupled to the second semi-rigid support; and a plurality of removable condyle pads stacked against one another and coupled to the hinge, an entirety of each of the plurality of removable condyle pads configured to be disposed entirely within a single spacing between the hinge and a knee of a patient to thereby provide the single spacing, wherein a single removable condyle pad of the plurality of removable condyle pads can be utilized at a time.

2. The brace of claim 1, further comprising: an elastomeric web framework coupled to the lateral upright and configured to secure an area of the knee of the patient when wearing the customizable knee brace; and a tensioning element comprising: a lace coupled to the elastomeric web framework and extending anterior of the first semi-rigid support and between the first semi-rigid support and the elastomeric web framework, and at least one reel element configured to adjust a tension in the lace, thereby increasing at least an amount of vertical tension of the elastomeric web framework, wherein each of the tensioning element and the single spacing provided by the plurality of removable condyle pads stacked against one another is configured to individually adjust a tension of the elastomeric web framework and thereby simultaneously is configured to offload a portion of a load on a desired compartment of the knee and provide a desired degree of extension assist to the knee.

3. The brace of claim 2, wherein the elastomeric web framework comprises silicone.

4. The brace of claim 2, wherein, when under tension, the elastomeric web framework is configured to both customize a fit of the brace around the knee of the patient and redistribute at least a portion of a load from a medial compartment of the knee of the patient.

5. The brace of claim 2, wherein the elastomeric web framework comprises a plurality of interconnected elastomeric segments that define at least one alignment opening configured to receive a patellar portion of the knee of the patient.

6. The brace of claim 1, wherein:
the thigh cuff is formable and configured to conform to a thigh of the patient; and
the shin cuff is formable and configured to conform to a shin of the patient.

7. The brace of claim 1, wherein the thigh cuff and the shin cuff are heat-formable in a temperature range at least partially overlapping 160-180 degrees Fahrenheit.

8. The brace of claim 1, further comprising a formable pad configured to provide cushioning to a thigh or shin of the patient.

9. The brace of claim 1, further comprising at least one strap configured to wrap around at least a posterior portion of the knee of the patient thereby securing the brace to the patient.

10. A kit for providing a customizable knee brace for use in treatment of osteoarthritis, the kit comprising: the customizable knee brace, comprising: a lateral upright comprising: a first semi-rigid support, a second semi-rigid support, and a hinge physically coupling the first semi-rigid support and the second semi-rigid support; a thigh cuff coupled to the first semi-rigid support; a shin cuff coupled to the second semi-rigid support; and a plurality of removable condyle pads stacked against one another and coupled to the hinge, an entirety of each of the plurality of removable condyle pads configured to be disposed entirely within a single spacing between the hinge and a knee of a patient, wherein a single removable condyle pad of the plurality of removable condyle pads can be utilized at a time; the kit further comprising a plurality of heating pads configurable to heat at least one of the thigh cuff for forming to the patient's thigh and the shin cuff for forming to the patient's shin.

11. The kit of claim 10, wherein the customizable knee brace further comprises: an elastomeric web framework coupled to the lateral upright and configured to secure an area of the knee of the patient when wearing the customizable knee brace; and a tensioning element comprising: the plurality of removable condyle pads, a lace coupled to the elastomeric web framework and extending anterior of the first semi-rigid support and between the first semi-rigid support and the elastomeric web framework, and at least one reel element configured to adjust a tension in the lace, thereby increasing at least an amount of vertical tension of the elastomeric web framework; wherein each of the tensioning element and the single spacing provided by the plurality of removable condyle pads stacked against one another is configured to individually adjust a tension of the elastomeric web framework and thereby simultaneously is configured to offload a portion of a load on a desired compartment of the knee and provide a desired degree of extension assist to the knee.

12. The kit of claim 11, wherein, when under tension, the elastomeric web framework is configured to both customize a fit of the brace around the knee of the patient and redistribute at least a portion of a load from a medial compartment of the knee of the patient.

13. The kit of claim 11, wherein the elastomeric web framework comprises a plurality of interconnected elastomeric segments that define at least one alignment opening configured to receive a patellar portion of the knee of the patient.

14. The kit of claim 11, wherein the desired compartment is configured to be a medial compartment of the knee of the patient.

15. The kit of claim 10, wherein the thigh cuff and the shin cuff are heat-formable in a temperature range at least partially overlapping 160-180 degrees Fahrenheit.

16. The kit of claim 10, further comprising at least one strap coupled to the lateral upright and configured to wrap around at least a posterior portion of the knee of the patient thereby securing the brace to the patient.

17. The kit of claim 10, further comprising packaging configured to reduce or eliminate alteration of a shape of any portion of the customizable knee brace during transit within the kit.

18. A method for treating osteoarthritis utilizing a customizable knee brace, the method comprising: forming a thigh cuff of the customizable knee brace to conform to a thigh of a patient; forming a shin cuff of the customizable knee brace to conform to a shin of the patient, wherein the customizable knee brace further comprises a lateral upright comprising at least: a first semi-rigid support, a second semi-rigid support, a hinge physically coupling the first semi-rigid support and the second semi-rigid support, and stacking a plurality of removable condyle pads against one another and coupling the plurality of removable condyle pads to the hinge, an entirety of each of the plurality of removable condyle pads being disposed entirely within a single spacing between the hinge and a knee of the patient, wherein a single removable condyle pad of the plurality of condyle pads can be utilized at a time.

19. The method of claim 18, further comprising: securing an area of the knee of the patient utilizing an elastomeric web framework that is coupled to the lateral upright; and individually and collectively adjusting a tension of the elastomeric web framework utilizing each of the plurality of removable condyle pads and a tensioning element comprising a reel and a lace by: carrying out the stacking of the plurality of removable condyle pads against one another and coupling the plurality of removable condyle pads to the hinge, and utilizing the reel to adjust a tension in the lace, which is coupled to the elastomeric web framework and extends anterior of the first semi-rigid support and between the first semi-rigid support and the elastomeric web framework, wherein the individually and collectively adjusting the tension of the elastomeric web framework simultaneously offloads a portion of a load on a desired compartment of the knee and provides a desired degree of extension assist to the knee.

20. The method of claim 19, wherein the utilizing the reel to adjust the tension in the lace of the tensioning element increases an amount of vertical tension in the elastomeric web framework.

\* \* \* \* \*